United States Patent [19]

Riess et al.

[11] Patent Number: 5,399,694
[45] Date of Patent: Mar. 21, 1995

[54] FLUOROALKYLATED AMPHIPHILIC LIGANDS AND THEIR METALLIC COMPLEXES

[75] Inventors: Jean G. Riess; Pierre Vierling, both of Falicon; Nathalie Garelli, Nice, all of France

[73] Assignee: Application et Transferts de Technologies Avancees, Nice, France

[21] Appl. No.: 955,473

[22] Filed: Oct. 2, 1992

[30] Foreign Application Priority Data

Oct. 2, 1991 [FR] France .................. 91 12130

[51] Int. Cl.[6] .............. C07F 17/02; C07F 17/00; C07F 15/00; C07D 401/04
[52] U.S. Cl. ........................... 546/2; 546/8; 546/258
[58] Field of Search ............... 546/2, 258, 8

[56] References Cited

U.S. PATENT DOCUMENTS 4,584,316  4/1986  Rosenberg et al. ............ 514/492

FOREIGN PATENT DOCUMENTS 1482811  4/1967  France .
9202291  2/1992  WIPO .

OTHER PUBLICATIONS

Freise, J., et al. Pharmacokinetics of liposome encapsulated cisplatin in rats. Arch. Int. Pharmacodyn. 258:180–192 (1982).
Khokhar, A. R., et al. Toxicity and anti–tumor activity of hydrophobic . . . Anti-cancer Drug Design. 3:177–184 (1988).
Garelli N., et al. Synthesis of new amphiphilic perfluoroalkylated bipyridines. J. Org. Chem. 57:3046–3051 (1992).
Teicher, B. A., et al. Effect of various oxygenation conditions and Fluosol-DA on cancer chemotherapeutic agents. Chem. Abstract 109: 163089u vol. 109, p. 31 (1988).
Garelli et al., Inorg. Chim. Acta., 194(2), 247–53 (1992).

Primary Examiner—Marianne M. Cintins
Assistant Examiner—Phyllis G. Spivack
Attorney, Agent, or Firm—Knobbe, Martens, Olson & Bear

[57] ABSTRACT

Fluoroalkylated amphiphilic ligands of bipyridine (I) that form complexes with platinum and palladium are disclosed.

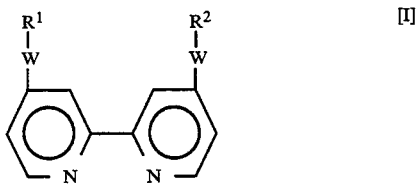

wherein $R^1$ and $R^2$ are independently a hydrogen atom, or a fluoroalkylated or hydrocarbon chain, provided at least one of $R^1$ and $R^2$ is a fluoroalkylated chain, and W represents a methylene, ester, ether, carbonyl or amide group.

12 Claims, 4 Drawing Sheets

FLUOROALKYLATED AMPHIPHILIC LIGANDS AND THEIR METALLIC COMPLEXES

This application claims priority to French application No. 91-12130, filed Oct. 2, 1991.

BACKGROUND OF THE INVENTION

The present invention relates to bidentate ligands that are capable of forming complexes with various metallic centers such as platinum, palladium and ruthenium. It relates particularly to ligands that can form metal-containing complexes that are transportable in vivo by liposomes or injected fluorocarbon emulsions.

It is indeed known that numerous transition metal complexes, particularly palladium and platinum complexes, have a chemotherapeutic activity, as described in U.S. Pat. No. 4,584,316. However, the complexes used at present have a therapeutic index (efficacy/toxicity ratio) which is still too low. Their excessive toxicity limits their use, notably on account of the risk of renal lesions.

One way of reducing this major disadvantage is to "isolate" these complexes by incorporation into or association with a vector, permitting a slower diffusion of the active principal. The encapsulation into liposomes of cis-platinum (Freise, J., W. H. Mueller, P. Magerstedt, H. J. Schmoll (1982) Arch. Int. Pharmacodyn., 258,180) and analogs thereof (Khokhar, A. R., S. Al-Baker, R. Perez-Soler (1988) Anticancer Drug Design 3, 177), reduces the efficacy of these agents, but improves the therapeutic index, prolongs their action, favorably modifies their biodistribution, and even promotes the induction of an antitumor activity against resistant tumors. However, the insertion of the known complexes into the lipidic membrane of the vector is not totally satisfactory, because the present ligands of these complexes are not sufficiently hydrophobic.

SUMMARY OF THE INVENTION

The invention provides compounds that are useful in improving the therapeutic efficacy of chemotherapeutic agents comprising a transition metal complex. The compounds are fluoroalkylated bidentate aminated ligands corresponding to one of the formulas

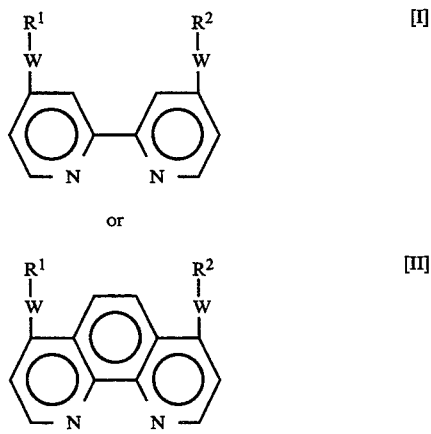

for which the bipyridine or phenanthroline group has the substituents $R^1$, $R^2$, and W as defined herein. $R^1$ is a radical comprising both a hydrocarbon region and a fluorinated hydrocarbon region; $R^2$ is a hydrocarbon radical, and W is a chemical linking group, such as for example, a methylene or carboxyl group.

The invention also provides a method of synthesizing the ligands by reacting a bipyridine or phenanthroline of the formula

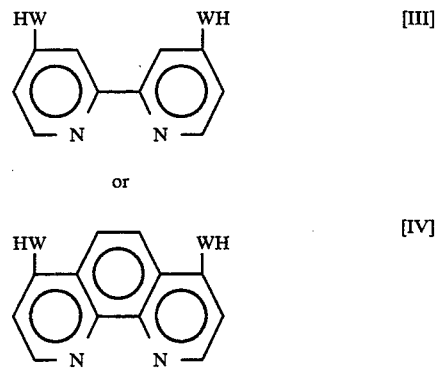

where W is O or $CH_2$, with a compound of formula $R^4V$ wherein $R^4$ represents a hydrocarbon radical and V represents a leaving group, and reacting the products of formula (V–VIII) with an iodide of the formula $R_FI$ to yield the amphiphilic bidentate fluorinated ligand. The invention also provides methods of synthesis for starting bipyridine or phenanthroline compounds wherein W is —C(O)O—, —C(O)—N ($R^3$)—, —O—C(O)—, —N($R^3$)—C—(O)—, or —C(O)—.

The invention also provides complexes of transition metal with the bidentate ligands of the invention, wherein the complexes have the general formula LM(II or IV) $A^1xA^2y(H_2O)_z$ or $[LM(II)OH]_xA^3$ wherein L is the ligand of (I) or (II) and M is a metal. In a preferred embodiment, M is platinum or palladium.

According to other aspects of the invention, the ligand or complex is incorporated into vesicles or liposomes. The ligands may also be present in an emulsion, wherein the emulsion comprises an oily phase, an aqueous phase and a surfactant. In a preferred embodiment of this aspect of the invention, the oily phase of the emulsion is a fluorocarbon.

According to yet another aspect of the invention, there are provided pharmaceutical formulations comprising emulsions or other formulations containing the fluorinated bidentate ligands of the invention.

DETAILED DESCRIPTION OF THE INVENTION

Figure 1:
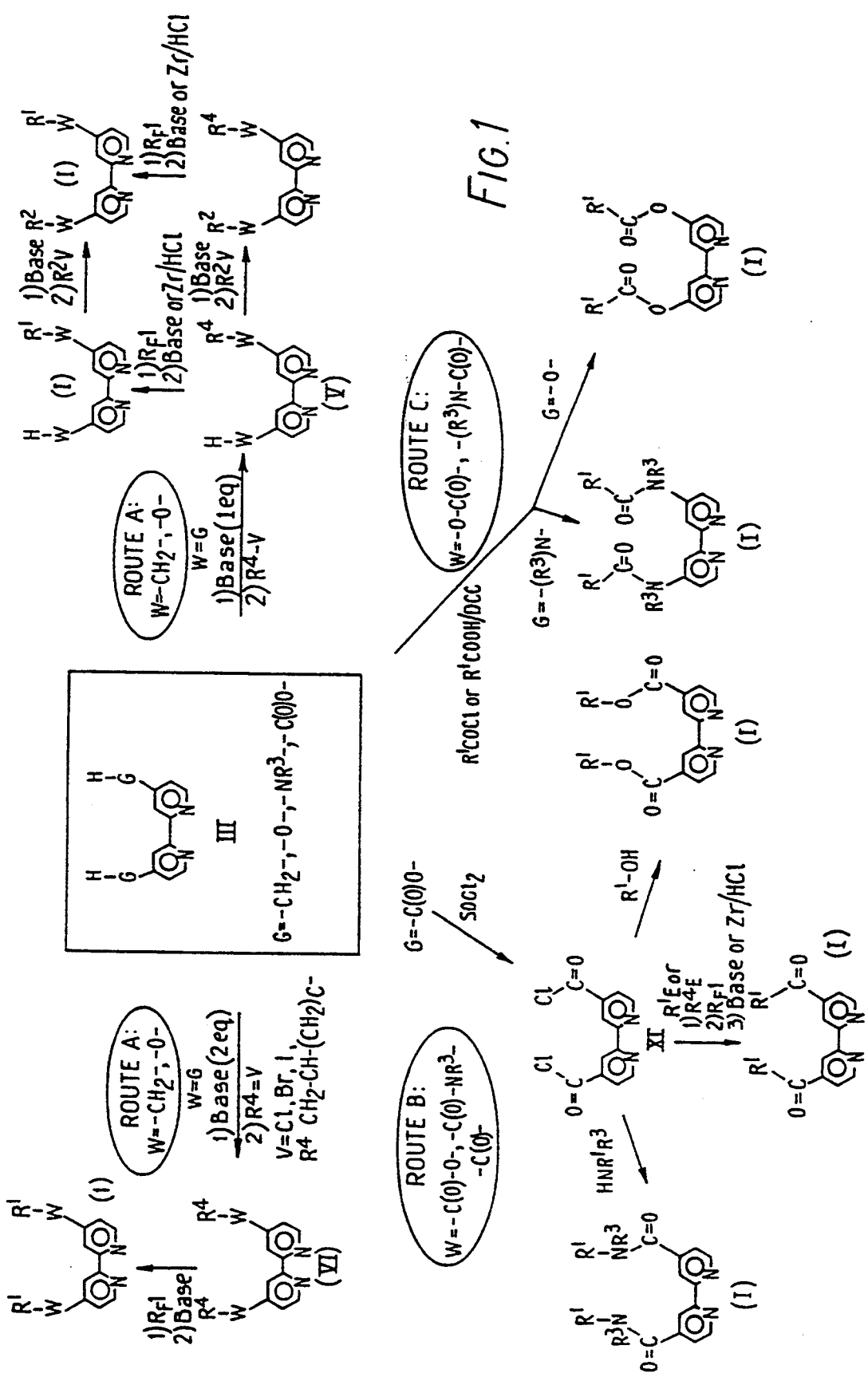
FIG. 1 represents the synthetic routes to the different ligands of the invention, taking as an example the bipyridine nucleus.
Figure 2:
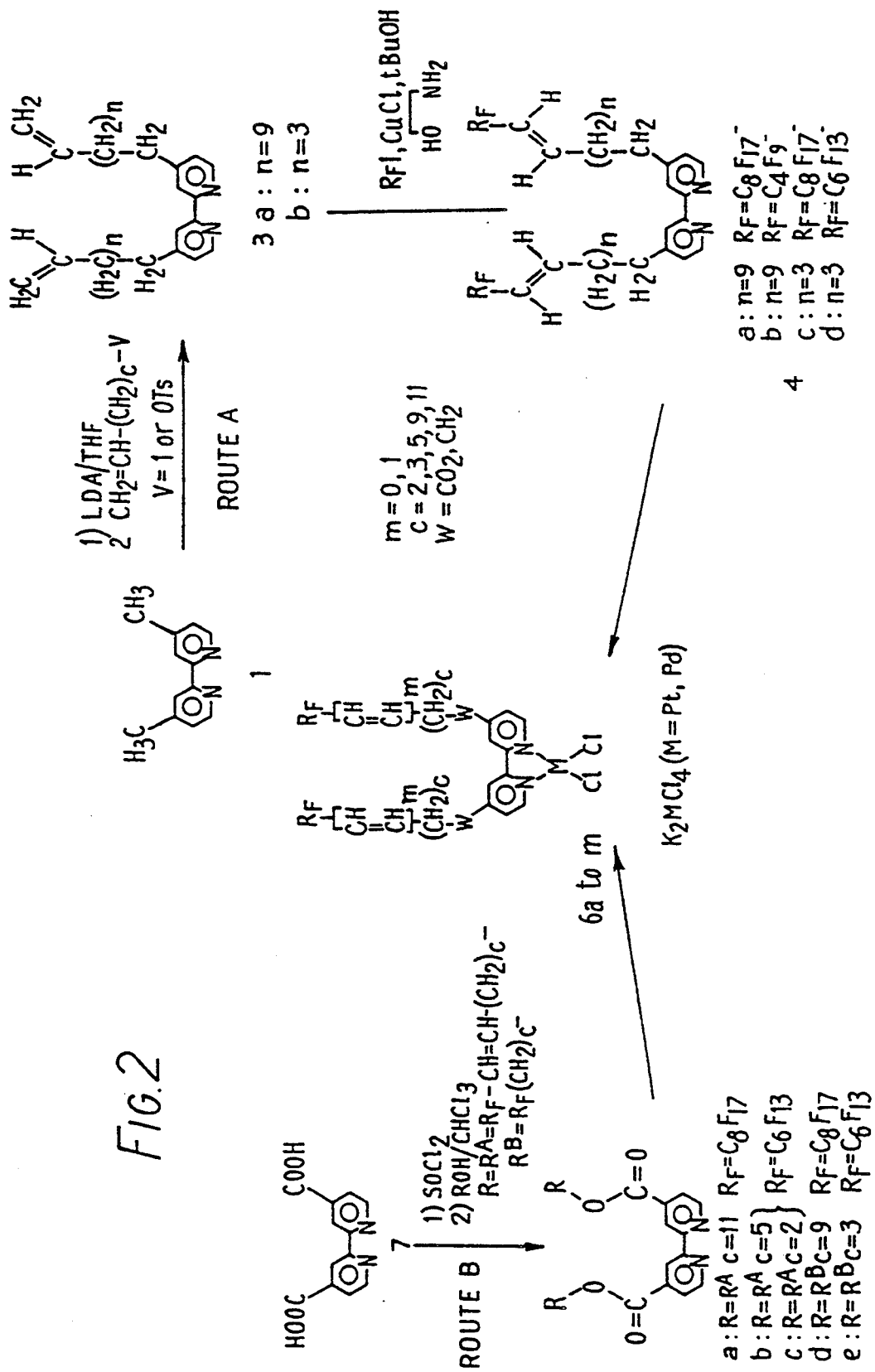
FIG. 2 represents the synthetic schemes corresponding to Examples 1 to 22.
Figure 3:
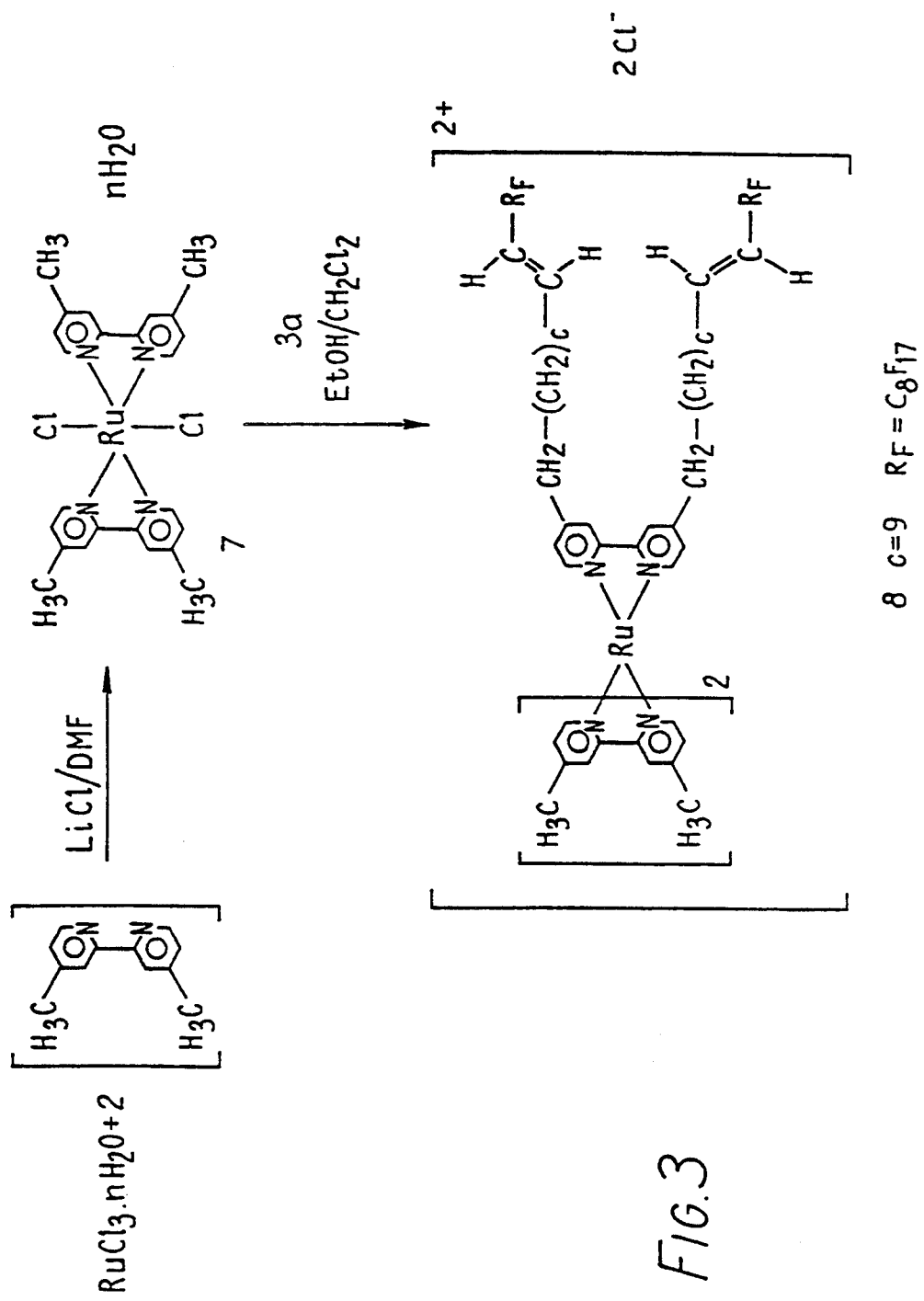
FIG. 3 is the synthetic scheme of the ruthenium complex of Example 23.
Figure 4:
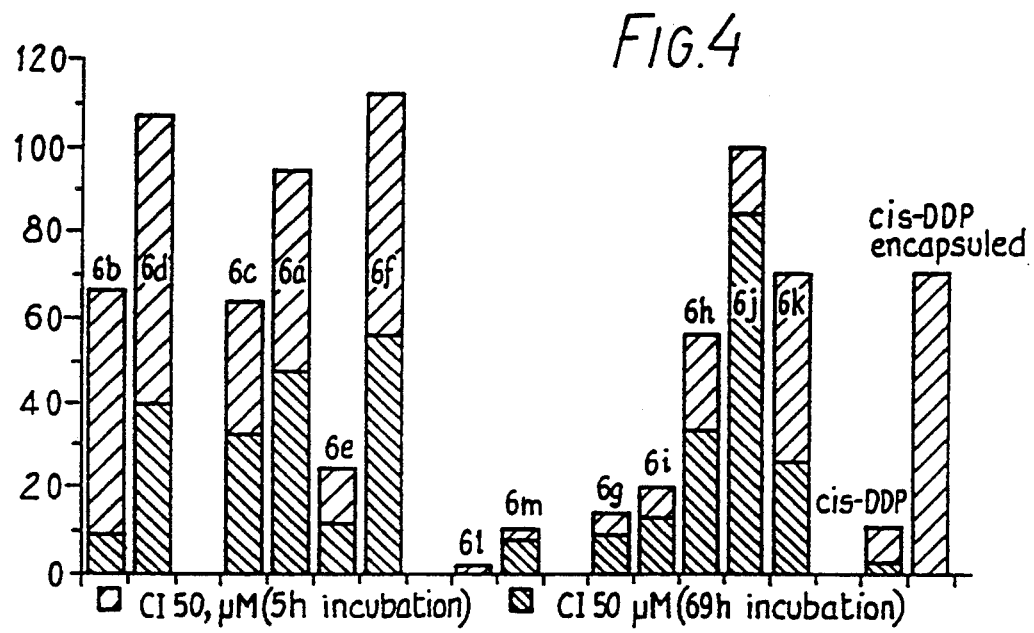
FIG. 4 is a diagram illustrating the anti-tumor activity of the complexes of the invention, expressed in $CI_{50}$, i.e. the concentration in complex for which 50% of the cellular growth is inhibited, (in $\mu$mol/l) after 5 h of incubation and after 69 h of incubation.
Figure 5:
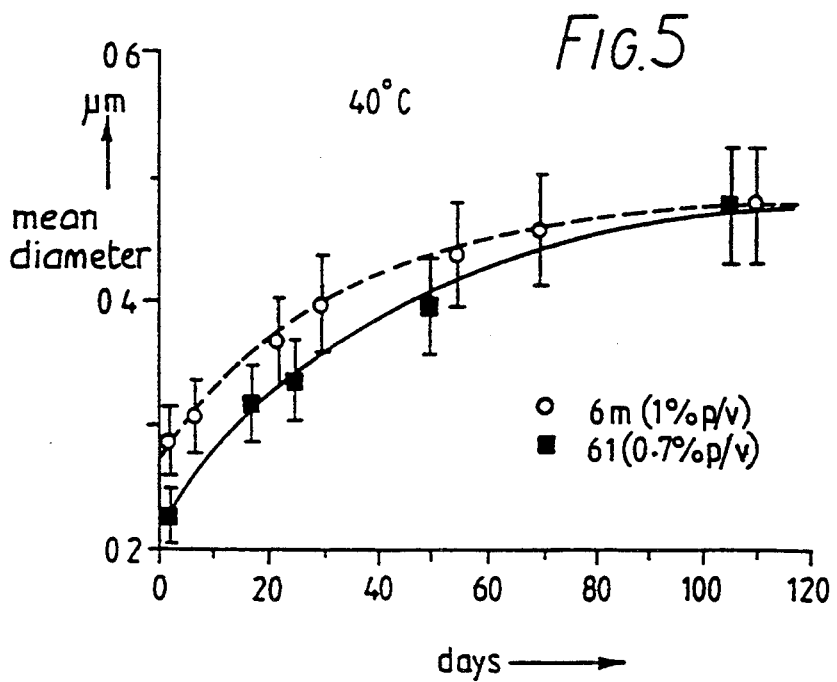
FIG. 5 is a diagram representing the evolution of the average dimensions (in $\mu$m) of the particles of emulsions of example 25, as a function of time, in days, during tests of ageing at 40° C.

The object of the invention is to provide strongly amphiphilic, fluoroalkylated ligands derived from aromatic amines which, when present in platinum or palladium complexes, improve the insertion of the complexes into the lipid membrane of vectors, such as liposomes, or other dispersions such as emulsions, which permit a slow diffusion of the complex.

The incorporation of these complexes into fluorocarbon emulsions achieves the combined advantages of the slow diffusion of therapeutic agent obtained by the use of a vector with the capacity of fluorocarbons to deliver oxygen into hypoxic, radioresistant, and chemoresistant zones of solid tumors, and thus to increase the efficacy of the treatment.

Such a synergistic effect has been demonstrated (Teicher, B. A., N. L. McIntosh-Lowe, N. L. Rose; Biomaterials, Artificial Cells, Artificial Organs (1988), 16-1-3 533) with certain alkylating, antimetabolic or antibiotic agents when used with a fluorocarbon emulsion under oxygen atmosphere.

In addition, the use of fluorocarbon emulsions instead of liposomes for this purpose is of interest, because the intravascular persistence of the fluorocarbon droplets is distinctly longer than that of liposomes and the droplets tend to accumulate around the tumors. Such ligands and the complexes formed from them can be used preferably for the transport and vectorization of medicinal substances based on transition metals, and as antimicrobial, antiviral, antifungal and antitumoral agents.

The fluoroalkylated ligands of the invention are derived from aromatic amines of the bipyridine or phenanthroline types. According to the invention, the fluoroalkylated bidentate aminated ligand can be formulated as:

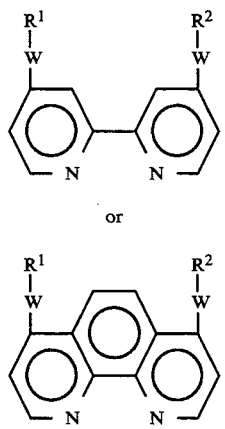

in which
1) W is a bivalent group chosen from among
   a) —$CH_2$—,
   b) —O—C(O)—,
   c) —C(O)—O—
   d) —O—,
   e) —C(O)—,
   f) —$NR^3$—C(O)—, and
   g) —C(O)—$NR^3$—,
with $R^3$ representing a hydrogen atom or a linear or branched, saturated or unsaturated hydrocarbon radical, having 1 to 24 carbon atoms, 2) $R^1$ is a radical chosen from among radicals of the formula:
   a) $R_F$—$(CH_2)_a$—$(CH=CH)_b$—$(CH_2)_c$—$(CH=CH)_d$—$(CH_2)_e$—
      a being a whole number from 0 to 12,
      b being a whole number from 0 to 12,
      c being a whole number from 0 to 11,
      d being a whole number from 0 to 12,
      e being a whole number from 0 to 11,
      b+d=0 to 12, and
      c+e=0 to 11,
   b) $R_F$—$(CH_2CH_2O)_f$—$CH_2$—
   c) $R_F$—$[CH(CH_3)CH_2O]_f$—$CH_2$—
   d) $R_F$—$(CH_2CH_2S)_f$—$CH_2$— f being a whole number from 1 to 12, wherein $R_F$ is a branched, cyclic, or linear fluorinated alkyl radical of from 2 to 23 carbon atoms, in which 50 to 100% of the hydrogen atoms have been replaced by fluorine atoms, provided $R_F$ comprises at least 4 fluorine atoms, and optionally, $R_F$ can bear other substituents chosen from Cl and Br.

3) $R^2$ represents
   a) a hydrogen atom,
   b) $R^1$, or
   c) a radical chosen from among the radicals of formula
      $R_H$—$(CH_2)_a$—$(CH=CH)_b$—$(CH_2)_c$—$(CH=CH)_d$—$(CH_2)_e$—
      $R_H$—$(CH_2CH_2O)_f$—$CH_2$—
      $R_H$—$(CH(CH_3)CH_2O)_f$—$CH_2$—, or
      $R_H$—$(CH_2CH_2S)_f$—$CH_2$— wherein $R_H$ is a hydrogen atom or a saturated or unsaturated, linear or branched hydrocarbon radical of from 1 to 24 carbon atoms, and a, b, c, d, e and f are as defined above.

The ligands corresponding to formulae (I) and (II) above have the advantage of bearing, on one hand, a coordinating hydrophilic head formed by bipyridine or phenanthroline and, on the other hand, at least one fluoroalkylated chain which confers on them the property of being both hydrophobic, thus favoring their insertion into the lipid membranes of the liposomes, and fluorophilic, allowing their incorporation into fluorocarbon emulsions. In addition, because they can bear a long fluorophilic fluoroalkylated chain ($R^1$) and a long lipophilic hydrocarbon chain ($R^2$), they can be easily incorporated into fluorocarbon or hydrocarbon emulsions or some other oily phase using hydrocarbon surfactants (such as egg yolk phospholipid, or pluronic) or fluoroalkylated or perfluoroalkylated surfactants.

According to the invention, the fluorinated alkyl radical $R_F$ which confers this fluorophilicity on the ligand can be chosen, for example, from among the radicals of formulae:
   a) $F(CF_2)_i$— wherein i is a whole number from 2 to 12,
   b) $(CF_3)_2CF$—$(CF_2)_j$— wherein j is a whole number from 0 to 8,
   c) $R_{F1}[CF_2CF(CF_3)]_k$— wherein $R_{F1}$ represents $CF_3$—, $C_2F_5$—, or $(CF_3)_2CF$— and k is a whole number from 1 to 4,
   d) $R_{F2}(R_{F3})CFO(CF_2)$n wherein $R_{F2}$ and $R_{F3}$ independently represent $CF_3$—, $C_2F_5$—, n—$C_3F_7$— or $CF_3CF_2CF(CF_3)$—, wherein $R_{F2}$ and $R_{F3}$ together form —$(CF_2)_4$— or —$(CF_2)_5$—, and n is a whole number from 1 to 6,
   e) $CF_3CF_2O(CF_2CF_2O)_tCF_2$— wherein t is a whole number from 0 to 5, f) $CF_3(CF_2)_2O[CF(CF_3)CF_2O]_u-CF(CF_3)-$,
wherein u is a whole number from 0 to 6, and g) the radicals of paragraphs a) to f) wherein one or more fluorine atoms are replaced by one or more hydrogen, chlorine or bromine atoms, provided that at least 50% of the atoms bound to the carbon skeleton of $R_F$ are fluorine atoms and that RF contains at least 4 fluorine atoms.

Among the fluorine radicals corresponding to the above formulae, the radical of formula $F(CF_2)_i-$ in which i is a whole number from 2 to 12, and preferably from 3 to 9, is preferred.

In the present text the term "hydrocarbon radical" applies to saturated, monounsaturated and polyunsaturated hydrocarbon radicals, the unsaturations being either ethylenic or acetylenic, and the radicals being linear, branched or cyclic.

Generally, in the ligands of the invention, the fluoroalkylated chain represented by $R_F$ is bound to the nucleus of the aromatic amine by a hydrocarbon chain which can comprise ethylenic unsaturations, etheroxide functional groups or thioether functional groups.

In a preferred embodiment of the invention, the highly fluorinated radical $R_F$ is bound to the aromatic nucleus by the intermediary of a hydrocarbon radical which can bear ethylenic unsaturations. Thus, in this preferred embodiment, $R^1$ is a radical of the formula:

$R_F-(CH_2)_a-(CH=CH)_b-(CH_2)_c-$, wherein $R_F$, a, b, and c are as defined above.

In this preferred embodiment, $R^2$ can represent the same radical as $R^1$, either a hydrogen atom, or a hydrocarbon radical of formula $R_H-(CH_2)_a-(CH=CH)_b-(CH_2)_c-$ wherein $R_H$, a, b and c are as defined above.

In this preferred embodiment, W advantageously represents the group $CH_2-$ or $-C(O)-O-$.

Methods of Synthesis

The present invention also provides procedures for preparing the fluoroalkylated ligands described above. The procedure depends in particular on the nature of the W group.

Thus, when W represents $-CH_2-$ or $-O-$, the ligand of formula (I) or (II) can be prepared by a procedure consisting of:

a) provoking the reaction of the mono- or the dianion derived from a bipyridine or a phenanthroline of formula:

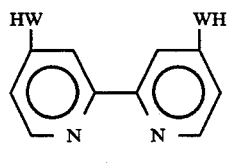

[III]

or

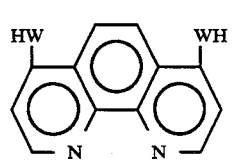

[IV]

wherein W is O or $CH_2$, with a compound of formula $R^4V$ wherein $R^4$ represents a radical of formula $CH_2=CH-(CH_2)_c-(CH=CH)_d-(CH_2)_e-$,
wherein c, d and e are as defined above; and V is a leaving group known to chemists, such as a halogenide, tosylate, mesylate, etc., and b) provoking the reaction of the compound or compounds of formulae:

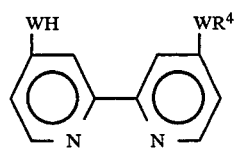

[V]

or

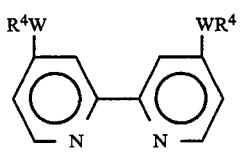

[VI]

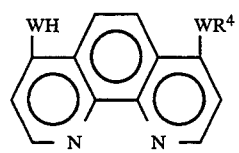

[VII]

or

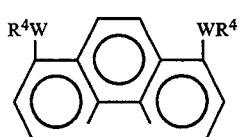

[VIII]

obtained in step a) with an iodide of formula $R_FI$ in which $R_F$ has the above definition.

This procedure can be followed in particular to obtain a ligand of formula (I) or (II) wherein $R^1$ contains a fluoroalkylated radical and $R^2$ represents H or $R^1$. When $R^2$ represents H, the mono-anion of the bipyridine of formula (III) or of the phenanthroline of formula (IV) is made to react in order to provoke the reaction of the compound of formula $R^4V$ with only one W group of the aromatic base.

Generally a mixture is obtained, and it is necessary at the end of the reaction to isolate the required ligand.

When a ligand of formula (I) or (II) is required, wherein W represents $CH_2$ or O, $R^1$ is a fluoroalkylated radical and $R^2$ is a hydrocarbon radical corresponding to the formulae given in paragraph 3c) concerning the definition of $R^2$ given above, it is possible to provoke the reaction, in the first step, of the anion derived from compounds of formula (V) or (VII) with a compound of formula $R^2V$ wherein $R^2$ represents a hydrocarbon radical such as those defined in 3c) for $R^2$ and V is a leaving group as defined above, to form the compound or compounds of formulae

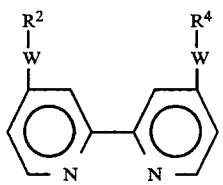

or

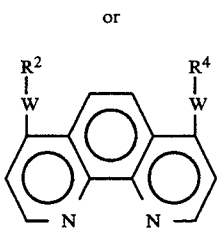

then, to allow to react, in a second step, an iodide of formula $R_FI$ ($R_F$ having the above definition) with compounds of formula (IX) or (X), which transforms the $R^4$ W group into a $R^1$ W group, the order of these two steps being reversible.

Ligands of formula (I) or (II) with W representing $CH_2$ or O, $R^1$ being a fluoroalkylated radical and $R^2$ a hydrogen radical such as defined above, can also be prepared by allowing a compound of formula (I) or (II) wherein $R^2$ represents H, $R^1$ is a fluoroalkylated radical and W is $CH_2$ or O, to react with a hydrocarbon radical of formula $R^2V$, wherein $R^2$ is a hydrogen radical such as defined above and V is a leaving group.

When W represents —C(O)—O—, ligands of formula (I) or (II) wherein $R^2$ is identical to $R^1$, bearing such a —C(O)—O— group, can be prepared by a procedure consisting of allowing a bipyridine or a phenanthroline of formula

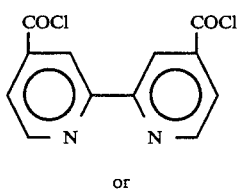

or

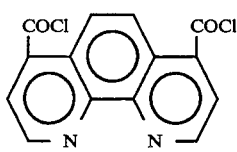

to react with an alcohol of formula $R^1OH$ wherein $R^1$ has the above definition.

The starting reactant, acid chloride of bipyridine or phenanthroline, can be prepared from bipyridine or phenanthroline of formula

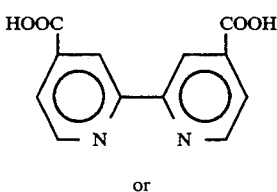

or

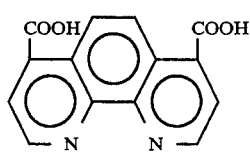

by reaction with $SOCl_2$.

The fluorinated alcohols of formula $R^1OH$ used as starting products in this procedure are commercially available (Sigma, St. Louis, Mo.) or can be prepared by classical procedures.

When W represents —C(O)—N($R^3$), the fluorinated ligand of formula (I) or (II) wherein $R^2$ is identical to $R^1$, can be prepared by a procedure comprising allowing a bipyridine or a phenanthroline of formula (XI) or (XII) to react with a fluoroalkylated alkylamine of formula $R^1$—N($R^3$)H wherein $R^1$ and $R^3$ have the above definition.

The fluoroalkylated amines used as starting products in this procedure are also commercially produced (Sigma, St. Louis Mo.), or can be prepared by classical procedures.

When W represents C(O)—, the ligand of formula (I) or (II) of the invention, wherein $R^2$ is identical to $R^1$, can be prepared by a procedure consisting of allowing a bipyridine or a phenanthroline of formula (XI) or (XII) to react with a compound of formulae $R^1E$, $R^4E$, $(R^1)_2G$, $(R^4)_2G$, $R^1GX^0$ or $R^4GX^0$ wherein $R^1$ and $R^4$ have the above signification, E represents Li, Na or K, G is Mg, Zn, Cd or Hg, and $X^0$ is a halogen, given that the compounds issued from reactions with reactives containing the $R^4$ radical are, in a second step, made to react with an iodide $R_FI$ to transform them into compounds containing the $R^1$ radical.

When W represents —OC(O)—, the ligand of formula (I) or (II) of the invention wherein $R^2$ is identical to $R^1$ can be prepared by a procedure consisting of allowing a bipyridine or a phenanthroline of formula:

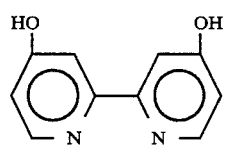

or

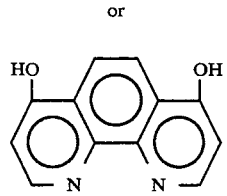

to react with a compound of formula $R^1COR^5$ wherein $R^1$ has the above definition and $R^5$ represents OH or Cl.

This reaction is effected in the presence of a coupling agent, for example dicyclohexylcarbodiimide, when $R^5$ is OH.

The starting reagent, perfluoroalkylated acids or acid chlorides $R^1COR^5$, are commercial products (Fluorochem Limited, Derbyshire SK 139RY) or can be prepared by classical procedures.

When W represents —N($R^3$)—C(O)—, the ligand of formula (I) or (II) wherein $R^2$ is identical to $R^1$ can be prepared by a procedure comprising allowing a bipyridine or a phenanthroline of formula:

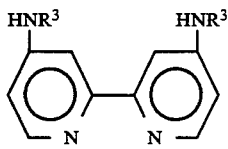

or

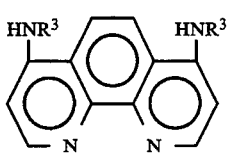

to react with a compound of formula $R^1COR^5$ wherein $R^1$, $R^3$ and $R^5$ have the above signification.

In the attached FIG. 1, the preparation procedures for the ligands of the invention, described above, have been regrouped, using the compounds bearing the bipyridine motif as an example.

The fluoroalkylated amphiphilic ligands of the invention can be used in particular in complexes of platinum, palladium or ruthenium.

In addition, the invention concerns platinum or palladium complexes of formula:

LM(II or IV) $A^1xA^2y(H_2O)_z$ or $[LM(II)OH]_xA^3$ in which

1) L represents the ligand of formula (I) or (II) described above,
2) M is platinum or palladium,
3) $A^1$ is a monovalent anionic ligand,
4) $A^2$ is a bivalent anionic ligand
5) x, y and z are such that
   x=0, 1, 2, 3 or 4
   y=0, 1 or 2
   z=0 or 2
   x+2y=2 when the oxidation state of M is II; or
   x+2y=4 when the oxidation state of M is IV; and the degree of coordinance (2+x+2y+z) is equal to 4 or 6
6) $A^3$ represents two $A^1$ ligands or an $A^2$ ligand when x is 2, three $A^1$ ligands or a trianionic ligand when x is 3, and four $A^1$ ligands or two $A^2$ ligands when x is 4, and the $A^1$ can be different monovalent anions when $x \geq 2$, and the $A^2$ different bivalent anions when y=2.

In these complexes, the platinum or the palladium is preferably in oxidation state II, i.e. x+2y=2. In addition, these complexes when dispersed in water can undergo dissociation of one or several valence M-A1 or M-A2 bonds, leading to ionic species of formula:

$[LMA^1_{x-n}A^2_{z-m}(H_2O)_{z+n+m}]^{(n+m)+}nA^1,mA^2$ with $0 \leq n \leq x$ and $0 \leq m \leq y$.

The invention also concerns ruthenium complexes bearing the ligands of the invention, the complexes having the formula:

$(L^1_\alpha L^2_\beta L^3_\gamma, RuA^1_{x1}1A^2_{y1})^{q+}$ $q/v$ $Z^{v-}$ wherein 1) $L^1$ represents the ligand of formula (I) or (II) described above,
2) $L^2$ represents a neutral bidentate amine ligand,
3) $L^3$ represents a neutral monodentate amine ligand, $H_2O$ or $NH_3$,
4) $A^1$ is a monovalent anionic ligand,
5) $A^2$ is a bivalent di-anionic ligand,
6) Z is $A^1$ or $A^2$,
7) v is the charge of the anion Z, and
8) $\alpha$, $\beta$, $\gamma$, x1, y1, v and q are such that
   $\alpha$=1, 2 or 3
   $\beta$=0, 1 or 2
   $\gamma$=0, 1, 2, 3 or 4
   x1=0, 1 or 2
   y1=0 or 1
   $2\alpha+2\beta+\gamma+x1+2y1=6$
   v=1 or 2
   q=2-x1-2y1
   x1+2y1=0, 1 or 2.

In the above formula, the bidentate amine ligands that can be used for $L^2$ can be aliphatic, cycloaliphatic or aromatic. Examples of such ligands are 1,2-diaminopropane, 1,3-diaminopropane, 1,2-diaminocyclohexane, 2,2'-bipyridine, 4,4'-dimethyl-2,2'-bipyridine, 1,10-phenanthroline, 1,2-diaminoethane, 1,2-diaminobenzene, imidazole, pyrimidine, 3-amino-pyridine, 1,4-diaminobutane, 1,2-diaminocyclopentane, o-phenylenediamine , 5, 6-diaminopyrimidine, 2,3-diaminonaphthalene, 1,2 -diaminocycloheptane, 1,2 -diaminocyclooctane, diamino-2-methylpropane, nitro-phenylenediamine, 1,3-diamino-2 propanol, 2,3-diaminopyridine, 3,4-diaminotoluene, 1,2-dianilinoethane, 4-carboxyphenylenediamine, 2-amino-4 picoline, 3-aminoquinoline, 1,5-diaminopentane.

It is preferable to use aromatic bidentate ligands of bipyridine or phenanthroline.

The monodentate neutral amine ligands that may be used for $L^3$ can be, for example, alkylamines in which the alkyl radical bears 1 to 4 carbon atoms, for example the methyl-, ethyl-, n-propyl, isopropyl- and n-butyl-amines; arylamines such as aniline; arylalkylamines such as benzylamine; lower hydroxyalkyl amines such as ethanolamine, propanolamine; lower alkoxy amines such as methoxylamine; lower alkoxy, lower alkyl amines such as methoxymethylamine; heterocyclic amines such as pyridine and aziridine; and aminoacids of formula $R^6$—$CHNH_2$—$COOH$ in which $R^6$ is a hydrogen atom, an lower alkyl radical, an lower hydroxyalkyl or an lower arylalkyl radical.

In palladium, platinum and ruthenium complexes, the monovalent anionic ligands susceptible of being used for $A^1$, $A^3$ or Z can be of different types.

As examples, anionic ligands can be used chosen from the group comprising chlorides, bromides, iodides, nitrites, nitrates, carboxylates, lactates, alkoxy, aryloxy, hydrides, fluorides, acetates, trifluoroacetates, chloroacetates, cyanates, thiocyanates, azides, chlorites, hypochlorites, hypophosphites and hydroxides.

In the different complexes of the invention, the bivalent anionic ligands which can be used for $A^2$, $A^3$ or Z can be chosen, for example, from the group comprising malonates, oxalates, pyrophosphites, dithiooxalates, phthalates, carboxyphthalates, gluconates, glucuronates, carbonates, sulfites, selenites, pyrosulfites, dithionites, sulfates, isocitrates and ascorbates.

The trivalent ligands susceptible of being used for $A^3$ can be chosen, for example, from the group comprising phosphates, arsenite, orthoarsenate or ferricyanide.

In the invention, bivalent anionic ligands, coordinated in monodentate fashion, can also be used, but in this case, they are considered as monovalent $A^1$ anionic ligands.

In the case of platinum or palladium complexes, it is generally preferable to use complexes corresponding to the formula LMA$^1$$_2$ in which A$^1$ is, for example, a chloride anion; these are cis-platinum II or palladium II complexes.

In the case of ruthenium complexes, these can comprise only one bivalent anionic ligand or two monovalent anionic ligands, and the other ligands are constituted by the L$^1$ ligand of the invention or by one or two bidentate neutral amine ligands and/or two or four monodentate neutral aminated ligands. In ruthenium complexes, it is also possible to use only neutral ligands, constituted by either the L$^1$ ligands of the invention, or by L$^1$ ligands of the invention with other monodentate and/or bidentate neutral ligands.

Platinum or palladium complexes corresponding to the formula:

$$LMA^1_xA^2_y$$

wherein L, M, A$^1$ and A$^2$ have the above definition and in which x+2y=2, can be prepared by reaction of K$_2$MCl$_4$ with the ligand L to form the complex LMCl$_2$, i.e. the complex LMA$^1$$_2$ with A$^1$ representing Cl—.

In the case of platinum or palladium complexes corresponding to oxidation state IV of the metal, these can be prepared by reaction of K$_2$MCl$_6$ with the ligand L to form the complex LMCl$_4$, i.e. the complex LMA$^1$$_4$ with A$^1$ representing Cl.

If it is desired to change the nature of the anion, the chloride ions of complexes LMCl$_2$ or LMCl$_4$ can be exchanged for other A$^1$ or A$^2$ anions, for example by putting the complex in contact with a salt bearing these anions, e.g. silver nitrate in the case where A$^1$ is NO$_3$.

Ruthenium complexes of formula:

$$(L_{60}{}^1L_\beta{}^2L_{65}{}^3RuA^1{}_{x1}A^2{}_{y1})^{q+}\; q/v\; Z^{v-}$$

can be prepared by reaction of ruthenium trichloride RuCl$_3$, nH$_2$O with one of the ligands L$^1$, L$^2$ or L$^3$ to form the complex of formula L$^1$$_2$RuCl$_2$; L$^2$$_2$RuCl$_2$; L$^2$$_4$RuCl$_2$; or L$^3$$_4$RuCl$_2$.

When this complex does not bear the ligand L$^1$ of the invention, this can be included by substituting the ligand L$^1$ of the invention for the chloride anions of the complex, for example to form the complex of formula:

$$[L^1L^2{}_2Ru]^{2+}\; 2Cl-, \text{ or}$$

$$[L^1L^3{}_4Ru]^{2+}\; 2Cl-$$

When it is desired to form a complex bearing anions other than Cl−, the Cl− anions are exchanged for other anions by putting complex L$^1$$_2$RuCl$_2$ into contact with an appropriate salt.

The ligands and complexes of the invention are of considerable interest for numerous applications, for they possess diverse properties linked to the presence of both the bipyridine or phenanthroline polar head and the fluoroalkylated chain of the ligand, and to the nature of the metal present in the complex. The complexes are, in particular, antitumor agents.

Thus, a further object of the present invention consists in preparations for therapeutic use bearing at least one complex or ligand of the invention.

These preparations can be in the form of solutions (including micelies), dispersions (liposomes, niosomes, vesicules), gels, emulsions, microemulsions in water or any other appropriate solvent, and phases with a structure similar to that of microemulsions containing an oil or polar or non-polar substances, tablets, suppositories, sugar-coated pills, capsules, pills. These preparations can be administered in the usual ways : orally, anally, locally, parenterally, intravenously, intraperitoneally and intramuscularly.

The ligands and complexes of the invention can also be used alone, but it is generally preferable to include them in diverse preparations (micelies, vesicles, liposomes, emulsions, for example), sometimes associating them with at least one other active principle or active pharmaceutical substance, for example with other antitumoral agents known to practitioners, in order to form a synergy of their therapeutic activity.

Thus, following an early method of realization, the preparation is an emulsion bearing at least one ligand or complex of the invention.

By "emulsion" any preparation comprizing an oily phase, an aqueous phase and one or more surfactant(s) is intended.

In this type of emulsion, the surfactants used can be lecithins, copolymers of alkylene oxide, for example of polyoxyethylene and polyoxopropylene, or any other natural or synthetic hydrocarbon or fluoroalkylated surface-active product.

In these emulsions, the oily phase can be a hydrocarbon or, preferably, a fluorocarbon or highly fluorinated compound, or a mixture of such fluorocarbon compounds, susceptible of serving, for example, in the transport of gases such as oxygen. The fluorocarbons and highly fluorinated compounds can be, for example, linear or cyclic compounds, with molecular weights preferably from 400 to 700, chosen from among the following compounds: 1,2-bis(F-alkyl)-ethenes and more particularly 1,2-bis(F-butyl)-ethene (F-44E), perfluorodecalin, the perfluoromethyldecalins, the perfluoromethyl- and the perfluorodimethyladamantanes, the perfluoromethyl-, perfluorodimethyl-, and perfluorotrimethylbicyclo(3,3,1)nonanesandtheir-homologues, the perfluoroperhydrophenanthrenes, the ethers of formulae: (CF$_3$)$_2$CFO(CF$_2$CF$_2$)$_2$OCF(CF$_3$)$_2$, (CF$_3$)$_2$CFO(CF$_2$CF$_2$)$_3$OCF—(CF$_3$)$_2$; (CF$_3$)$_2$CFO(CF$_2$CF$_2$)$_2$F; (CF$_3$)$_2$CFO(CF$_2$CF$_2$)$_3$F; F[CF(CF$_3$)CF$_2$O]$_2$CHFCF$_3$; F[CF(CF$_3$)CF$_2$O]$_3$CHFCF$_3$; (CF$_3$CF$_2$CF$_2$(CF$_2$)$_u$)$_2$O, wherein u=1,3 or 5; amines N(C$_3$F$_7$)$_3$; N(C$_4$F$_9$)$_3$; the perfluoromethylquinolidines, perfluoro-N-perhydroquinolines and perfluoro-N-methylperhydroisoquinolines; the halogen derivatives C$_6$F$_{13}$Br; C$_8$F$_{17}$Br (PFOB); C$_{10}$F$_{21}$Br; C$_6$F$_{13}$CBr$_2$CH$_2$Br; 1-bromo perfluoroisopropyl-4 cyclohexane; C$_8$F$_{16}$Br$_2$; and CF$_3$CF$_2$CF$_2$—C(CF$_3$)$_2$—CH$_2$CH$_2$CH$_2$—CF(CF$_3$)$_2$ or CF$_3$O(CF$_2$CF$_2$O)$_u$CF$_2$—CH$_2$OH, wherein u=2 or 3.

In the emulsion, the oily phase, constituted for example by a fluorocarbon or highly fluorinated compound, can represent from 10 to 125% in weight/volume of the emulsion. Generally the emulsion contains from 0.01 to 30% w/v of a surfactant and from 6 to 40 mmol of complex per mol of surfactant.

The aqueous phase may contain other additives, including inorganic salts, generally in the form of buffers, in order to adjust the pH and oncotic and osmotic pressures, and to obtain an injectable isotonic composition.

According to a second method of realization, the ligand(s) or complex(es) of the invention are incorporated into other dispersed systems such as liposomes, niosomes, nanoparticles, in particular into natural or synthetic vesicles or liposomes. These vesicles or liposomes can be based on phospholipids.

The procedures for the preparation of the lipidic membranes, liposomes, nanoparticles or niosomes are well known to professionals and comprise techniques using solvents, injection, ultrasounds or mechanical high-pressure homogenizers such as the Gaulin homogenizer or a microfluidizer.

In the preparations comprizing liposomes, these can be formed from natural or synthetic lecithins, for example perfluoroalkylated lecithins, or from a mixture of natural and synthetic phospholipids including perfluoroalkylated phospholipids. In these liposome-based preparations, the compounds of the invention can be incorporated into a liposomal vehicle and the liposomes can be polymerized. Generally, the liposome-based preparations contain from 6 to 40 mmol of complex per mol of phospholipids.

The products and preparations of the invention, alone or in the form of solutions, gels, emulsions, dispersions, liposomes and microemulsions, can be used in human and veterinary medicine and in biology or as fungicides, or antimicrobe, antivirus and antitumor agents. If they are contained in fluorocarbon emulsions, their chemotherapeutic use can be coupled with radiotherapy under oxygen atmosphere.

Another field of potential application of the amphiphilic ligands and complexes of the invention consists in the constitution of dispersed systems functionalized as catalytic microreactors. Thus, the metallic complexes presented in this invention can also find their use 1) as catalyzers, supported or not, in reactions of hydrogenation, isomerization, hydroformylation, oxydating hydrolysis of olefins, carboxylation of methanol and activation of alcanes, and 2) considering the exceptional photoreductor properties of certain of the ligands presented and the photochemical and photophysical properties of their complexes, in systems linked to the conversion of light energy into chemical or electrochemical energy.

The present invention is described below in detail using the following examples with references to related FIGS. 1–5, but the chemical reactions described are disclosed in terms of their general application to the preparation of the ligands and ligand metal complexes of the invention. Occasionally, the reaction may not be applicable as described to each compound included within the disclosed scope of the invention. The compounds for which this occurs will be readily recognized by those skilled in the art. In all such cases, either the reactions can be successfully performed by conventional modifications known to those skilled in the art, e.g. by appropriate protection of interfering groups, by changing to alternative conventional reagents, or by routine modification of reaction conditions. Alternatively, other reactions disclosed herein or otherwise conventional will be applicable to the preparation of the corresponding compounds of the invention. In all preparative methods, all starting materials are known or readily preparable from known starting materials; all temperatures are set forth uncorrected in degrees Celsius; and, unless otherwise indicated, all parts and percentages are by weight.

EXAMPLES 1 AND 2

A. Synthesis of bis(a,w-alkenyl)bipyridines 2

1) di-(dodecenyl-11'')-4,4'-bipyridine-2,2' 2a:

To a solution of n-butyl-lithium 1.6M in hexane (45 mL) and di-isopropylamine (10 mL) in anhydrous tetrahydrofurane at 0° C., 5 g of 4,4'-dimethyl-2,2'-bipyridine 1 are added. After 3 h, iodo-10-undecene (15.4 g) is added. The reaction is stopped after 3 h by adding methanol, and the solution obtained is washed in iced water, then extracted with ether. The residue is chromatographed over silica gel. After evaporation and recrystallization in hexane, white crystals (6.93 g, 52%) of 2a are obtained. $^1$H RMN (CDCl$_3$): 4.78–5.14 (m, 4H, H$_2$C=), 5.47–6.07 (m, 2H, H—C=), 7.06 (dd, $^3$J$_{ortho}$=5.6 Hz, $^4$J$_{meta}$=1.5 Hz, 2H, H$_{5,5'}$), 8.27 (s large, 2H, H$_{3,3'}$), 8.52 (d, $^3$J$_{ortho}$=5.6 Hz, 2H, H$_{6,6'}$).

2) 4,4'-di- (5''-hexenyl )-bipyridine-2,2' 2b:

The protocol described above applied to di-isopropylamine ( 10 mL) n-butyl-lithium 1.6M (44.72 mL), to 5 g of 1 and to 18.8 g of p-toluene sulfonate of 4-pentenyl leads, after treatment and chromatography, to a colorless oil corresponding to 2b (5.47 g, 63%). $^1$H RMN (CDCl$_3$): 4.78–5.12 (m, 4H, H$_2$C=), 5.47–6.03 (m, 2H, H—C=), 7.10 (dd, $^3$J$_{ortho}$=6 Hz, $^4$J$_{meta}$=1.5 Hz, 2H, H$_{5,5'}$), 8.22 (s large, 2H, H$_{3,3'}$), 8.50 (d, $^3$J$_{ortho}$=6 Hz, 2H, H$_{6,6'}$)

B. Synthesis of bis-(F-alkyl-a,w-alkenyl)bipyridines 3

1) Compound 3a:

Compound 2a (4.7 g), F-octyl iodide (17.85 g), ethanolamine (2.5 mL), t-BuOH (10 mL) and CuCl (620 mg) are brought to reflux over 30 h under argon. After extraction with dichloromethane, washing with water, chromatography then recrystallization in dichloromethane, 3a is obtained (10.1 g, 79%). Anal. Calc. for C$_{50}$H$_{50}$F$_{34}$N$_2$: C, 45.43; H, 3.80; F, 48.75; N, 2.11. Found: C, 45.58; H, 3.98; F, 48.47; N, 2.12. $^1$H NMR (CDCl$_3$): 5.25–5.87 (m, 2H, =HC—CF2) , 6.15–6.60 (m, 2H, H—C=CH—CF$_2$), 7.13 (dd, $^3$J$_{ortho}$=5 Hz, $^4$J$_{meta}$=1.5 Hz, 2H, H$_{5,5'}$), 8.25 (s large, 2H, H$_{3,3'}$), 8 54 (d, $^3$J$_{ortho}$=5 Hz, 2H, H$_{6,6'}$). $^{19}$F NMR (CDCl$_3$): −82.5 (3F), −105.1, −112.8 (2F (cis/trans 10/90)), −123.5 (6F), −124.4 (2F), -125.3 (2F), −127.8 (2F).

2) Compound 3c:

The protocol described for the preparation of 3a, applied to 2b (4.31 g), F-octyl iodide (24.96 g), ethanolamine (2.43 mL), t-BuOH (13 mL) and CuCl (400 mg), leads, after chromatography and recrystallization in hexane, to 3c in the form of white crystals (7.76 g, 50%). Anal. Calc. for C$_{38}$H$_{26}$F$_{34}$N$_2$: C, 39.46; H, 2.26; F, 55.85; N, 2.42. Found: C, 39.75; H, 2.45; F, 56.22; N, 2.07. $^1$H NMR (CDCl$_3$): 5.50–5.70 (m, 2H, =HC—CF$_2$); 6.32–6.46 (m, 2H, H—C=CH—CF$_2$); 7.12 (dd, $^3$J$_{ortho}$=5 Hz, $^4$J$_{meta}$=1.3 Hz, 2H, H$_{5,5'}$); 8.26 (s large, 2H, H$_{3,3'}$); 8.57 (d, $^3$J$_{ortho}$=5 Hz, H$_{6,6'}$). $^{19}$F NMR (CDCl$_3$): −81.5 (3F); −106.9, −111.9 (2F (cis/trans 10/90)); −122.0 (2F); −122.2 (4F); −123.3 (2F); −124.0 (2F); −126.8 (2F).

EXAMPLE 3 di- [(F-butyl-12'')-dodecenyl-11'']-4,4'-bipyridine-2,2' 3b

The protocol described above applied to 2a (6.25 g), F-butyl iodide (14.93 g), ethanolamine (2.3 mL), t-BuOH (12 mL) and CuCl (280 mg) gives, after treatment, chromatography and recrystallization, white crystals of 3b (7 g, 62%) . Anal. Calc. for C$_{42}$H$_{50}$F$_{18}$N$_2$: C, 54.54; H, 5.45; F, 36.97; N, 3.03. Found: C, 54.41; H, 5.36; F, 36.29; N, 2.72. $^1$H NMR (CDCl$_3$): 5.24–5.94 (m, 2H, =HC—CF$_2$), 6.20–6.68 (m, 2H, H—C=CH—CF$_2$), 7.11 (dd, $^3$J$_{ortho}$=5 Hz, $^4$J$_{meta}$=1.5 Hz, $H_{5,5'}$), 8.23 (s large, 2H, $H_{3,3'}$), 8.55 (d, $^3J_{ortho}=5$ Hz, 2H, $H_{6,6'}$). $^{19}F$ NMR (CDCl$_3$): −82.8 (3F), −108.6, −113.1 (2F (cis/trans 12/88)), −126 (2F), −127.5 (2F).

EXAMPLE 4 di-[(F-hexyl-6'')hexenyl-5'']-4,4'-bipyridine-2,2' 3d

The protocol described above applied to 2b (2.67 g), F-hexyl iodide (18.64 g), ethanolamine (1.51 mL), t-BuOH (12 mL), CuCl (250 mg) gives, after chromatography and recrystallization, white crystals corresponding to 3d (4.43 g, 56%). Anal. Calc. for C$_{34}$H$_{26}$F$_{26}$N$_2$: C, 42.69; H, 2.74; F, 51.63; N, 2.92. Found: C, 42.33; H, 2.74; F, 52.63; N, 2.94. $^1H$ NMR (CDCl$_3$): 5.50–5.70 (m, 2H, =HC—CF$_2$); 6.30–6.50 (m, 2H, H—C=CH—CF$_2$); 7.13 (d, $^3J_{ortho}=5$ Hz, 2H, $H_{5,5'}$); 8.24 (s large, 2H, $H_{3,3'}$); 8.57 (d, $^3J_{ortho}=5$ Hz, $H_{6,6'}$). $^{19}F$ NMR (CDCl$_3$): −81.5 (3F); −111.9, −114.0 (2F (cis/trans 8/98)); −122.0 (2F); −123.6 (2F);−124.0 (2F); −126.8 (2F).

EXAMPLES 5 AND 9 di-[(F-octyl-11')-undecyloxycarbonyl]-4,4'-bipyridine-2,2' 5a di-[(F-hexyl-2'')-ethoxycarbonyl]-4,4'-bipyridine-2,2' 5b di-[(F-hexyl-5'')-pentyloxycarbonyl]-4,4'-bipyridine-2,2'5c di-[(F-octyl-11'')-undecenyloxycarbonyl-10'']-4,4'-bipyridine-2,2' 5d di-[(F-hexyl-5'')-pentenyloxycarbonyl-4'']-4,4'-bipyridine-2,2' 5e

Diacid 4 (525 mg) is suspended in SOCl$_2$ (8 mL) and brought to reflux until the diacid is completely solubilized. The excess of SOCl$_2$ is then eliminated by distillation, and the resulting powder is dissolved in anhydrous chloroform and added to a chloroform solution of (F-octyl)-11-undecanol (3.1 g) and NEt$_3$ (1.2 mL). The mixture is brought to reflux over 4 h and stirred at room temperature for 12 h. After evaporation of the chloroform, washing with water, filtration and recrystallization in dichloromethane, white crystals corresponding to 5a (3 g, 100%) are obtained. Anal. Calc. for C$_{50}$H$_{50}$F$_{34}$N$_2$O$_4$: C, 43.23; H, 3.63; F, 46.50; N, 2.02. Found: C, 43.02; H, 3.65; F, 46.27; N, 2.07. $^1H$ NMR (CDCl$_3$): 4.32 (t, $^3J_{H,H}=6.6$ Hz, 4H (H$_2$C)); 7.78 (dd, $^3J_{ortho}=5$ Hz, $^4J_{meta}=1.4$ Hz, 2H, $H_{5,5'}$); 8.75 (d, 2H, $^3J_{ortho}=5$ Hz, $H_{6,6'}$); 8.84 (s large, $^4J_{meta}=1.4$ Hz, 2H, $H_{3,3'}$) $^{19}F$ NMR (CDCl$_3$): −81.7 (3F); −114.5 (2F trans); −122.1 (6F), −123.0 (2F), −123.9 (2F); −126.5 (2F).

All the other compounds 5b to 5e are obtained from the respective alcohols, in the form of a white powder, with close-to-quantitative yields, by using this protocol.

Analysis of 5b:

Anal. Calc. for C$_{28}$H$_{14}$F$_{26}$N$_2$O$_4$: C, 36.13; H, 1.51; F, 52.75; N, 2.99. Found: C, 36.04; H, 1.55; F, 52.80; N, 2.69 $^1H$ NMR (CDCl$_3$): 4.72 (t, $^3J=6.5$ Hz, 4H (H$_2$C)$_{1''}$); 7.87 (dd, $^3J_{ortho}=5$ Hz, $^4J_{meta}=1.6$ Hz, 2H, $H_{5,5'}$), 8.86 (d, $^3J_{ortho}=5$ Hz, 2H, $H_{6,6'}$); 8.97 (s large, 2H, $H_{3,3'}$). $^{19}F$ NMR (CDCl$_3$): −81.2 (3F); −113.9 (2F trans); −122.3, −123.6 (10F); −126.6 (2F).

Analysis of 5c:

Anal. Calc. for C$_{34}$H$_{26}$F$_{26}$N$_2$O$_4$: C, 40.01; H, 2.57; F, 48.48; N, 2.74. Found: C, 38.98; H, 2.51, F, 48.34; N, 2.73. $^1H$ NMR (CDCl$_3$): 4.43 (t, $^3J_{H,H}=6.5$ Hz, 4H (H$_2$C)$_{1''}$); 7.91 (dd, $^3J_{ortho}=5$ Hz, $^4J_{meta}=1.6$ Hz, 2H, $H_{5,5'}$), 8.88 (d, $^3J_{ortho}=5$ Hz, 2H, $H_{6,6'}$); 8.95 (br.s, 2H, $H_{3,3'}$). $^{19}F$ NMR (CDCl$_3$): −81.3 (3F); −114.9 (2F trans); −122.4 (2F); −123.4 (2F); −124.2 (2F); −126.6 (2F).

Analysis of 5d:

Anal. Calc. for C$_{50}$H$_{46}$F$_{34}$N$_2$O$_4$: C, 43.62; H, 3.35; F, 46.64; N, 2.04. Found: C, 43.62; H, 3.25; F, 47.19; N, 2.04. $^1H$ NMR (CDCl$_3$): 4.41 (t, $^3J_{H,H}=6.5$ Hz, 4H, (H$_2$C)$_{1''}$); 5.41–5.77 (m, 2H, (H—C—CF$_2$); 6.33–6.54 (m, 2H, H—C=CH—CF$_2$); 7.89 (d, $^3J_{ortho}=5$ Hz, 2H, $H_{5,5'}$), 8.86 (d, $^3J_{ortho}=5$ Hz, 2H, $H_{6,6'}$); 8.97 (br.s, 2H, $H_{3,3'}$). $^{19}F$ NMR (CDCl$_3$): −81.2 (3F); −107.0, −111.7 (2F (cis/trans 13:87)); −121.9 (2F); −122.4 (4F); −123.2 (2F); −123.9 (2F); 126.6 (2F).

Analysis of 5e:

Anal. Calc. for C$_{34}$H$_{22}$F$_{26}$N$_2$O$_4$: C, 40.17; H, 2.18; F, 48.59; N, 2.76. Found: C, 40.08; H, 2.13; F, 48.38; N 2.69 $^1H$ NMR (CDCl$_3$): 4.41 (t, $^3J_{H,H}=6.5$ Hz, 4H, (H$_2$C)$_{1''}$); 5.51–5.90 (m, 2H, H—C—CF$_2$); 6.40–6.59 (m, 2H, H—C=CH—CF$_2$); 7.85 (dd, $^3J_{ortho}=5$ Hz, $^4J_{meta}=1.5$ Hz, 2H, $H_{5,5'}$), 8.82 (d, $^3J_{ortho}=5$ Hz, 2H, $H_{6,6'}$); 8.94 (br.s, 2H, $H_{3,3'}$). $^{19}F$ NMR (CDCl$_3$): −81.6 (3F); −107.3, −111.8 (2F (cis/trans 14:86); −122.0 (2F); −123.8 (2F); −124.2 (2F); −126.6 (2F).

EXAMPLES 10 AND 16 cis-dichloro-[di-[(F-octyl-12''')-dodecenyl-11'']-4,4'-bipyridine-2,2']platinum (II) 6a cis-dichloro-[di-[(F-octyl-12''')-dodecenyl-11'']-4,4'-bipyridine-2,2']palladium (II) 6b cis-dichloro-[di-[(F-butyl-12'') -dodecenyl-11'']-4,4'-bipyridine-2,2']platinum (II) 6c cis-dichloro-[di-[(F-butyl-12'')-dodecenyl-11'']-4,4'-bipyridine-2,2']palladium (II) 6d cis-dichloro-[di-[(F-octyl-6'')-hexenyl-5'']-4,4''-bipyridine-2,2']platinum (II) 6e cis-dichloro-[di-[(F-hexyl-6'')-hexenyl-5'']-4,4'-bipyridine-2,2']platinum (II) 6f cis-dichloro-[di-[(-F-hexyl-2'')-ethoxycarbonyl]-4,4'-bipyridine-2,2']platinum (II) 6h

A mixture of K$_2$PtCl$_4$ (II) (1.55 g) in a water/ethanol mixture (1:1) and compound 3a (3.40 g) in dichloromethane is brought to reflux under argon, until a colorless aqueous phase is obtained. The organic phase is filtered, evaporated to give a yellow powder which is washed with water and ethanol. The product is then purified by chromatography over silica gel using dichloromethane as eluent, and recrystallized in a dichloromethane/pentane/ethanol mixture to give a yellow powder corresponding to the expected product 6a (3.8 g, 95%). Anal. calc. for C$_{50}$H$_{50}$Cl$_2$F$_{34}$N$_2$Pt: C, 37.75; H, 3.16; Cl, 4.45; F, 40.60; N, 1.76; Pt, 12.26. Found: C, 37.87; H, 3.07; Cl, 4.11; F, 40.61; N, 1.70; Pt, 12.55. $^1H$ NMR (CDCl$_3$): 5.42–5.76 (m, 2H, =HC—CF$_2$), 6.31–6.52 (m, 2H, H—C=CH—CF$_2$), 7.16 (dd, $^3J_{ortho}=5$ Hz, $^4J_{meta}=1.5$ Hz, 2H, $H_{5,5'}$), 7.91 (s large, 2H, $H_{3,3'}$), 9.11 (d, $^3J_{ortho}=5$ Hz, 2H, $H_{6,6'}$) $^{19}F$ NMR (CDCl$_3$): −82.2 (3F), −107.2, −111.6 (2F (cis/trans 8.92)), −121.9 (2F), −122.4 (4F), −123.2 (2F), −124.0 (2F), −126.6 (2F). Complexes 6b to 6f and 6h (Examples 11 to 16) are obtained from the respective ligands and K$_2$MCl$_4$ (M=Pt or Pd), with 54–85% yields, by using this procedure.

Analysis of 6b:

Anal. calc. for C$_{50}$H$_{50}$Cl$_2$F$_{34}$N$_2$Pd: C, 39.98; H, 3.35; Cl, 4.72; F, 42.99; N, 1.86; Pd, 7.08. Found: C, 39.73; H, 3.29; Cl, 4.74; F, 42.70; N, 1.74; Pd, 6.93 $^1H$ NMR (CDCl$_3$): 2.87 (t, $^3J_{H,H}=7.5$ Hzm 4H, (H$_2$C)$_{1'''}$), 5.42–5.76 (m, H, =HC—CF$_2$), 6.32–6.54 (m 2H, H—C=CH—CF$_2$), 7.15 (dd $^3J_{ortho}=5$ Hz, $^4J_{meta}=1.5$ Hz, 2H, H$_{5,5'}$), 8.00 (s large, 2H, H$_{3,3'}$), 8.73 (d, $^3J_{ortho}$=5 Hz, 2H, H$_{6,6'}$) $^{19}$F NMR (CDCl$_3$): −81.4 (3F), −107.2, −111.7 (2F (cis/trans 8/92)), −122.0 (2F), −122.5 (4F), −123.3 (2F), −124.1 (2F), −126.7 (2F).

Analysis of 6c:

Anal. Calc. for C$_{42}$H$_{50}$Cl$_2$F$_{18}$N$_2$Pt: C, 42.36; H, 4.23; Cl, 5.95; F, 28.71; N, 2.35; Pt, 16.38. Found: C, 42.10; H, 4.26; Cl, 6.28; F, 28.69; N, 2.23; Pt, 15.84. $^1$H NMR (CDCl$_3$): 2.72 (t, 4H, $^3J_{H,H}$=8 Hz (H$_2$C)$_{1''}$), 5.43–5.78 (m, 2H, =HC—CF$_2$), 6.32–6.53 (m, 2H, H—C= CH—CF$_2$), 7.15 (dd, $^3J_{ortho}$=5 Hz, $^4J_{meta}$=1.5 Hz, H$_{5,5'}$), 7.94 (br.s, 2H, H$_{3,3'}$), 9.06 (d, $^3J$=5 Hz, 2H, H$_{6,6'}$). $^{19}$F NMR (CDCl$_3$): −81.7 (3F), −107.0, −111.9 (2F (cis/trans 10/90)), −124.8 (2F), −126.4 (2F).

Analysis of 6d:

Anal. Calc. for C$_{42}$H$_{50}$Cl$_2$F$_{18}$N$_2$Pd: C, 45.77; H, 4.57; Cl, 6.43; F, 31.03; N, 2.54; Pd, 9.65. Found: C, 45.79; H, 4.45; Cl, 6.47; F, 30.57; N, 2.64; Pd, 9.49. $^1$H NMR (CDCl$_3$): 2.87 (t, 4H, $^3J_{H,H}$=7.7 Hz (H$_2$C)$_{1''}$), 5.43–5.78 (m, 2H, =HC—CF$_2$), 6.32–6.53 (m, 2H, H—C= CH—CF$_2$), 7.15 (dd, $^3J_{ortho}$=6 Hz, $^4J_{meta}$=1.5 Hz, H$_{5,5'}$), 8.02 (s large, 2H, H$_{3,3'}$), 8.28 (d, $^3J_{ortho}$=6 Hz, 2H, H$_{6,6'}$). $^{19}$F NMR (CDCl$_3$): −81.6 (3F), −107.3, −111.9 (2F (cis/trans 12/88)), −124.9 (2F), −126.4 (2F).

Analysis of 6e:

Anal. Calc. for C$_{34}$H$_{26}$Cl$_2$F$_{26}$N$_2$Pt: C, 32.08; H, 1.84; Cl, 4.98; F, 45.41; N, 1.97; Pt, 13.71. Found: C, 32.20; H, 1.98; Cl, 5.51; F, 45.10; N, 2.07; Pt, 12.71.

Analysis of 6f:

Anal. Calc. for C$_{34}$H$_{26}$Cl$_2$F$_{26}$N$_2$Pt: C, 33.40; H, 2.14; Cl, 5.80; F, 40.40; N, 2.29; Pt, 15.96. Found: C, 32.92; H, 2.10; Cl, 5.42; F, 40.61; N, 2.28; Pt, 15.56. $^1$H NMR (CDCl$_3$): 2.84 (t, $^3J_{H,H}$=7.5 Hz 4H (H$_2$C)$_{1''}$); 5.48–5.82 (m, 2H, =HC—CF$_2$); 6.28–6.53 (m, 2H, H—C= CH—CF$_2$); 7.16 (d, ortho $^3J_{ortho}$=6 Hz, 2H, H$_{5,5'}$); 7.94 (s large, 2H, H$_{3,3'}$); 9.02 (d, $^3J_{ortho}$=6 Hz, H$_{6,6'}$). $^{19}$F NMR (CDCl$_3$): −81.3 (3F); −107.05, −111.7 (2F (cis/trans 4:96)); −122.2 (2F), −123.9 (2F), −124.2 (2F); −126.7 (2F).

Analysis of 6h:

Anal. Calc. for C$_{28}$H$_{14}$Cl$_2$F$_{26}$N$_2$O$_4$Pt: C, 29.96; H, 1.73; Cl, 5.89; F, 41.08; N, 2.33; Pt, 16.22. Found: C, 27.96; H, 1.25; Cl, 6.16; F, 40.57; N, 2.47; Pt, 14.76. $^1$H NMR (CDCl$_3$): 4.81 (t, $^3J_{H,H}$=6.5 Hz, 4H (H$_2$C)$_{1''}$); 8.08 (dd, $^3J_{ortho}$=5 Hz, $^4J_{meta}$=1.8 Hz, 2H H$_{5,5'}$); 8.57 (br.s, 2H, H$_{6,6'}$); 9.95 (d, 2H, $^3J_{ortho}$=6.6 Hz, H$_{3,3'}$). $^{19}$F NMR (CDCl$_3$): −81.3 (3F); −113.3 (2F trans); −121.8 (2F), −122.9 (2F), −123.6 (2F); −126.2 (2F).

EXAMPLES 17 TO 22 cis-dichloro-[di-[(F-octyl-11'')-undecyloxycarbonyl]-4,4'-bipyridine-2,2']platinum (II) 6g cis-dichloro-[di-[(-F-hexyl-5'')-pentyloxycarbonyl]-4,4'-bipyridine-2,2']platinum (II) 6i cis-dichloro-[di-[(F-octyl-11'')-undecenyloxy-10''-carbonyl]-4,4'-bipyridine-2,2']platinum (II) 6j cis-dichloro-[di-[(F-hexyl-5'')-pentenyloxy-4''-carbonyl]-4,4'-bipyridine-2,2']platinum (II) 6k cis-dichloro-[di-[(F-hexyl-5'')-pentyloxycarbonyl)]-4,4'-bipyridine-2,2']palladium (II) 6l cis-dichloro-[di-[(F-octyl-11'')-undecyloxycarbonyl)]-4,4'-bipyridine-2,2']palladium (II) 6m Ligand 5a (317 mg) in 50 mL of dichloromethane is added to a solution of K$_2$PtCl$_4$ (95 mg) and Et$_4$N$^+$Cl$^-$ (75.81 mg) in water. After reflux at 45° C. over 70 h, the organic phase is filtered and evaporated. The remaining powder is washed with pentane, then chromatographed over silica gel, by elution with dichloromethane. The yellow powder obtained is recrystallized in chloroform to give the expected complex 6g (230 mg, 60%). Anal. Calc. for C$_{50}$H$_{50}$Cl$_2$F$_{34}$O$_4$N$_2$Pt: C, 36.29; H, 3.04; Cl, 4.28; F, 39.03; N, 1.69; Pt, 11.79. Found: C, 36.53; H, 3.11; Cl, 4.15; F, 39.03; N, 1.70; Pt, 11.81. $^1$H NMR (CDCl$_3$): 4.48 (t, $^3J_{H,H}$=7 Hz, 4H (H$_2$C)$_{1''}$); 8.05 (dd, $^3J_{ortho}$=6 Hz, $^4J_{meta}$=1.5 Hz, 2H, H$_{5,5'}$); 8.59 (br.s, 2H, H$_{6,6'}$); 9.75 (d, $^3J_{ortho}$=6 Hz, 2H, H$_{3,3'}$) $^{19}$F NMR (CDCl$_3$): −81.1 (3F); −114.5 (2F), −120.0 (6F); −122.9 (2F); −123.7 (2F); −126.3 (2F).

Complexes 6i to 6m are obtained from the respective ligands and K$_2$MCl$_4$ (M=Pt or Pd), with 21–90% yields, by using this procedure.

Analysis of 6i:

Anal. Calc. for C$_{34}$H$_{26}$Cl$_2$F$_{26}$N$_2$O$_4$Pt: C, 31.74; H, 2.03; Cl, 5.51; F, 38.39; N, 2.20; Pt, 15.16. Found: C, 32.42; H, 2.09; Cl, 5.50; F, 38.37; N, 2.20; Pt, 15.09. $^1$H NMR (CDCl$_3$): 4.52 (t, $^3J_{H,H}$=7 Hz, 4H, (H$_2$C)$_{1''}$); 8.09 (dd, $_3J_{ortho}$=5 Hz, $^4J_{meta}$=1.5 Hz, 2H, H$_{5,5'}$); 9.13 (br.s 2H, H$_{6,6'}$); 9.75 (d, $^3J_{ortho}$=5 Hz, 2H, H$_{3,3'}$). $^{19}$F NMR (CDCl$_3$): −83.7 (3F); −117.2 (2F); −124.8 (2F); −125.8 (2F); −126.3 (2F), −128.9 (2F).

Analysis of 6j:

Anal. Calc. for C$_{50}$H$_{46}$Cl$_2$F$_{34}$N$_2$O$_4$Pt: C, 36.37; H, 2.81; Cl, 4.29; F, 39.13; N, 1.69; Pt, 11.81. Found: C, 36.97; H, 2.92; Cl, 4.11; F, 37.95; N, 1.62; Pt, 11.03. $^1$H NMR (CDCl$_3$): 4.48 (t, $^3J_{H,H}$=6.9 Hz, 4H, (H$_2$C)$_{1'}$); 5 56–5.54 (m, 2H, =HC—CF$_2$); 6.37–6.46 (m, 2H, H—C=CH—CF$_2$); 8.01 (dd, ortho $^3J_{ortho}$=6 Hz, $^4J_{meta}$=1.6 Hz, 2H, H$_{5,5'}$); 8.58 (br.s, 2H, H$_{6,6'}$); 9.57 (d, 2H, $^3J_{ortho}$=6 Hz, H$_{3,3'}$) $^{19}$F NMR (CDCl$_3$): −81.3 (3F); −107.2, −111.8 (2F (cis/trans 13:87)); −122.1 (2F), −122.5 (4F), −123.3 (2F); −124.1 (2F); −126.2 (2F).

Analysis of 6k:

Anal. Calc. for C$_{34}$H$_{22}$Cl$_2$F$_{26}$N$_2$O$_4$Pt: C, 31.84; H, 1.73; Cl, 5.53; F, 38.51; N, 2.18; Pt, 15.21. Found: C, 31.64; H, 1.81; Cl, 5.75; F, 37.20; N, 2.20; Pt, 13.80. $^1$H NMR (CDCl$_3$): 4.52 (t, $^3J_{H,H}$=6.5 Hz, 4H (H$_2$C)$_{1''}$); 5.65–5.90 (m, 2H H—C—CF$_2$); 6.46–6.54 (m, 2H, H—C=CH—CF$_2$); 8.03 (d, $^3J_{ortho}$=6 Hz, 2H, H$_{5,5'}$); 8.60 (br.s, H$_{6,6'}$); 9.63 (d, 2H, $^3J_{ortho}$=6 Hz, H$_{3,3'}$). $^{19}$F NMR (CDCl$_3$): −81.3 (3F); −107.3, −111.9 (2F cis/trans 10:90); −122.2 (2F), −123.4 (2F); −123.8 (2F); −126.7 (2F).

Analysis of 6l:

Anal. Calc. for C$_{34}$H$_{26}$Cl$_2$F$_{26}$N$_2$O$_4$Pd: C, 34.09; H, 2.19; Cl, 5.92; F, 38.39; N, 2.34; Pd, 8.89. Found: C, 33.88; H, 2.05; Cl, 5.38; F, 38.37; N, 2.43; Pd, 8.90. $^1$H NMR (CDCl$_3$): 4.52 (t, $^3J_{H,H}$=7 Hz, 4H, (H$_2$C)$_{1''}$); 8.00 (dd, $^3J_{ortho}$=6 Hz, $^4J_{meta}$=1.5 Hz, 2H, H$_{5,5'}$); 8.65 (br.s, 2H, H$_{6,6'}$); 9.52 (d, $^3J_{ortho}$=6 Hz, 2H, H$_{3,3'}$). $^{19}$F NMR (CDCl$_3$): −89.1 (3F); −114.8 (2F); −122.4 (2F); −123.4 (2F); −124.0 (2F); −126.5 (2F).

Analysis of 6m:

Anal. Calc. for C$_{50}$H$_{50}$Cl$_2$F$_{34}$O$_4$N$_2$Pd: C, 38.34; H, 3.22; Cl, 4.28; F, 41.24; N, 1.79; Pd, 6.79. Found: C, 37.99; H, 3.84; Cl, 4.15; F, 39.69; N, 2.23; Pd, 6.67. $^1$H NMR (CDCl$_3$): 4.48 (t, $^3J_{H,H}$=7 Hz, 4H, (H$_2$C)$_{1''}$); 8.18 (dd, $^3J_{ortho}$=6 Hz, $^4J_{meta}$=1.5 Hz, 2H, H$_{5,5'}$); 8.64 (br.s, 2H, H$_{6,6'}$); 9.56 (d, $^3J_{ortho}$=6 Hz, 2H, H$_{3,3'}$). $^{19}$F NMR (CDCl$_3$): −81.2 (3F); −114.9 (2F); −122.3 (6F); −123.2 (2F); −124.0 (2F); −126.6 (2F).

EXAMPLE 23 dichloride of
{di-[di-(dimethyl)-4,4'-bipyridine-2,2'][(di-(F-octyl-12")-dodecenyl-11")-4,4'-bipyridine-2,2']Ruthenium} 8

Ruthenium hydrate 7 (193 mg) and 2a (440 mg) in solution in an ethanol/dichloromethane mixture are brought to reflux in an anhydrous medium over 20 h. After evaporation, the powder obtained is dissolved in ethanol and filtered. The filtrate is then reduced to give the expected product 8, after washing with pentane, in the form of violet crystals (500 mg, 88%). Anal. Calc. pour $C_{74}H_{74}Cl_2F_{34}N_6Ru$: C, 47.64; H, 3.99; F, 34.63; N, 4.50. Found: C, 47.64; H, 3.99; F, 34.62; N, 4.50.

DISPERSIONS AND EMULSIONS:

The products described in this invention are active principles in anticancer chemotherapy, and are incorporated in liposomes or fluorocarbon emulsions. The dispersions (liposomes) are prepared by sonication, and the emulsions by high-pressure microfluidization. The ageing of the liposomes at 25° C. is followed by measuring the average size of the particles by light-diffusion (COULTER N4 SD), and the ageing of the emulsions is followed at 40° C. by measuring the average size of the particles by the centrifugal sedimentation method (HORIBA CAPA 700). The quantity of metal (platinum or palladium) incorporated in the liposomes is defined by dosage of the metal by atomic absorption, and the quantity of metal non-incorporated or rejected in time by the vesicles is dosed by atomic absorption of the metal in the supernatant after ultracentrifugation at 105000 g over 17 h at 4° C.

Dispersions Prepared with the Sonicator

EXAMPLE 24 formulation: complexes 6a to 6m $10^{-3}$ M;
egg-yolk phospholipids (EYP) $2\times10^{-2}$ M The compound and EYP in the form of dry film prepared by the chloroform film technique were dispersed in 12 mL of a saline phosphate buffer by sonication (BRANSON B30, probe 13 mm) in a Rosette cell at 40° C. The dispersion is then sterilized by filtration over a Millipore filter at 0.22 mm, or filtered at 0.22 mm then sterilized 15 min at 121° C. in an autoclave.

The evaluation of a cytotoxic activity requires the preparation of stable, homogeneous, reproducible, sterile, biocompatible samples. The tests were realized on dispersions of liposomes prepared from EYP in which these complexes were inserted. We have shown, amongst other things, that:

- the platinum and palladium complexes are not dispersible in water except in the presence of phospholipids;
- they become incorporated in liposomes formulated from EYP (average size of the liposomes: 50 to 140 nm) in the proportion of 6 to 40 mmoles/mole of EYP depending on the complex, which corresponds to an efficacy of incorporation of 10 to 100% (ratio quantity of complex incorporated/initial quantity for a given quantity of phospholipids);
- the preparations thus obtained are sterilizable (121° C., 15 min) and stable for at least seven months at room temperature (average size of the liposomes after sterilization and storage: 100 to 250 nm; no complex released in to the solution after 3 months;
- the molecular structure of the complexes is not altered by the conditions of preparation used (sonication, sterilization).

These results contrast with those reported in the literature for cis-platinum: whereas similar quantities can be encapsulated in liposomes (for an efficacy of encapsulation of 10 to 70%, depending on the formulation of the liposomes and their technic of preparation), the preparations obtained are usually unstable (a large quantity of complex is released into the solution after a few days, even when these preparations are kept at 4° C.).

Antitumor Activity

The evaluation of the antitumor activity of the perfluoroalkylated amphiphile complexes presented in the invention was realized in vitro on cell cultures issued from a human tumor line CAL27 which is sensitive to cis-platinum. Our complexes are tested encapsulated in liposomes of EYP for exposure times with the cell medium from 2 to 120 hours, the results being measured after 5 days. The cytotoxicity is given in $IC_{50}$ (a concentration in complex for which 50% of the cell growth is inhibited). Non-encapsulated cis-platinum is taken as reference. The results are given in FIG. 4.

All the liposomes bearing the platinum and palladium complexes presented in the invention present an antitumor activity on CAL 27; this activity increases with the exposure time 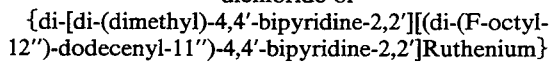. As an example, for 5 hours' exposure, 11 of the 13 encapsulated complexes of the invention tested present $IC_{50}$ of from 1 to 100 mM, and those of the other two are about 120–150 mM; for an exposure time of 69 hours ■), their $IC_{50}$ are reduced by half.

Nine of these complexes have an antitumor activity comparable to that of cis-platinum when it is encapsulated in vesicles of phospholipids [the efficacy of free cis-platinum is 1 to 10 times higher (IC 50=10 mM), but its therapeutic index is far better, and its action is prolonged when it is used in the encapsulated form].

Emulsions Prepared with the Microfluidizer

EXAMPLE 25

Formulation 61 0.7% w/v or 6m 1% w/v;
EYP 4% w/v and PFOB 90% w/v.

To prepare 40 mL of a 90% w/v concentrated emulsion of perfluorooctyl bromide (PFOB), the mixed 6m or 6l/EYP film is first dispersed at 15° C. in 19.6 mL of saline phosphate buffer by means of the ultraturrax at 8000 turns/min. The fluorocarbon (36 g) is then added over 4 min and the whole is mixed for 10 min at 24000 t/min. The pre-emulsion obtained is immediately transferred into a microfluidizer (MICROFLUIDICS model M110) kept at 15° C. and emulsified for 6 periods of 1 min with a break of 2 min between each period at 800–1000 bars. The emulsion is sterilized for 15 min at 100° C. in an autoclave. The results are presented in FIG. 5.

The fluorocarbon-concentrated emulsions thus presented containing the complexes of the invention are stable for at least 120 days at 40° C.

It is believed that one skilled in the art can, using the preceding description, utilize the invention to its fullest extent. The invention may be embodied in other specific forms without departing from its spirit or essential restrictive, and the scope of the invention is, therefore, indicated by the appended claims rather than by the foregoing description. All modifications which come within the meaning and range of the lawful equivalency of the claims are to be embraced within their scope.

What is claimed is:

1. A fluoroalkylated bidentate aminated ligand corresponding to the formula

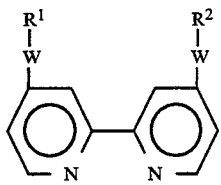

wherein
1) W is a bivalent group chosen from the group consisting of:
   a) —$CH_2$—,
   b) —O—C(O)—,
   c) —C(O)—O—
   d) —O—,
   f) —$NR^3$—C(O)—, and
   g) —C(O)—$NR^3$—,
   wherein $R^3$ is a hydrogen atom or a linear or branched, saturated or unsaturated hydrocarbon radical, having 1 to 24 carbon atoms;
2) $R^1$ is a radical selected from the group consisting of:
   a) $R_F$—$(CH_2)_a$—$(CH=CH)_b$—$(CH_2)_c$—$(CH=CH)_d$—$(CH_2)_e$—
      wherein a is a whole number from 0 to 12;
      b is a whole number from 0 to 12;
      c is a whole number from 0 to 11;
      d is a whole number from 0 to 12;
      e is a whole number from 0 to 11;
      b +d=0 to 12; and
      c +e=0 to 11;
   b) $R_F$—$(CH_2CH_2O)_f$—$CH_2$—
   c) $R_F$—$[CH(CH_3)CH_2O]_f$—$CH_2$—
   d) $R_F$—$(CH_2CH_2S)_f$—$CH_2$—
      wherein f is a whole number from 1 to 12;
      wherein $R_F$ is a branched, cyclic, or linear fluorinated alkyl radical of from 2 to 23 carbon atoms in which 50 to 100% of the hydrogen atoms have been replaced by fluorine atoms, and $R_F$ comprises at least 4 fluorine atoms, and optionally can bear other substituents chosen from Cl and Br;
3) $R^2$ represents
   a) a hydrogen atom,
   b) $R^1$, or
   c) a radical selected from the group consisting of:
      $R_H$—$(CH_2)_a$—$(CH=CH)_b$—$(CH_2)_c$—$(CH=CH)_d$—$(CH_2)_e$—
      $R_H$—$(CH_2CH_2O)_f$—$CH_2$—
      $R_H$—$(CH(CH_3)CH_2O)_f$—$CH_2$—, or
      $R_H$—$CH_2CH_2S)_f$—$CH_2$—
      wherein $R_H$ is a hydrogen atom or a saturated or unsaturated, linear or branched hydrocarbon radical of from 1 to 24 carbon atoms, and a, b, c, d, e and f are as defined above.

2. A ligand according to claim 1, wherein $R_F$ is selected from the group consisting of:
   a) F$(CF_2)_i$— wherein i is a whole number from 2 to 12,
   b) $(CF_3)_2CF$—$(CF_2)_j$— wherein j is a whole number from 0 to 8,
   c) $R_{F1}[CF_2CF(CF_3)]_k$— wherein $R_{F1}$ represents $CF_3$—, $C_2F_5$— or $(CF_3)_2CF$— and k is a whole number from 1 to 4,
   d) $R_{F2}$ ($R_{F3}$)CFO$(CF_2)_n$ wherein $R_{F2}$ and $R_{F3}$ independently represent $CF_3$—, $C_2F_5$—, n—$C_3F_7$—or $CF_3CF_2CF(CF_3)$—, or wherein $R_{F2}$ and $R_{F3}$ together form —$(CF_2)_4$— or —$(CF_2)_5$—; and n is a whole number from 1 to 6;
   e) $CF_3CF_2O(CF_2CF_2O)_tCF_2$— wherein t is a whole number from 0 to 5;
   f) $CF_3(CF_2)_2O[CF(CF_3)CF_2O]_u$—$CF(CF_3)$— wherein u is a whole number from 0 to 6; and
   g) the radicals of paragraphs a) to f) wherein one or more fluorine atoms are replaced by one or more hydrogen, chlorine or bromine atoms, provided that at least 50% of the atoms bound to the carbon skeleton of $R_F$ are fluorine atoms and that $R_F$ contains at least 4 fluorine atoms.

3. A ligand according to claim 1, wherein W represents —$CH_2$— or —C(O)—O—.

4. A ligand according to any of claims 1, 2 or 3, wherein $R^1$ and $R^2$ represent a radical of formula:

$R_F$—$(CH_2)_a$—$(CH=CH)_b$—$(CH_2)_c$ wherein $R_F$, a, b and c are as defined in claim 1.

5. A ligand according to any of claims 1, 2 or 3, wherein $R^1$ represents the radical of formula:

$R_F$—$(CH_2)_a$—$(CH=CH)_b$—$(CH_2)_c$— and $R^2$ represents a hydrogen atom or the radical of formula:

$R_H$—$(CH_2)_a$—$(CH=CH)_b$—$(CH_2)_c$ wherein $R_F$—, $R_H$, a, b and c are as defined in claim 1.

6. A ligand according to claim 1, selected from the group consisting of:
4,4'-di-[(12"-F-octyl) -11"-dodecenyl]-2,2'-bipyridine;
4,4'-di[(6"-F-octyl)-5"-hexenyl]-2,2'-bipyridine;
4,4'-di-[(6"-F-hexyl)-5"-hexenyl]-2,2'- bipyridine;
4,4'-di-[(11"-F-octyl)-undecyloxycarbonyl]-2,2'-bipyridine;
4,4'-di-[(2"-F-hexyl)-ethoxycarbonyl]-2,2'-bipyridine;
4,4'-di-[(5"-F-hexyl)-pentyloxycarbonyl]-2,2'-bipyridine;
4,4'-di[(11"-F-octyl)-10"-undecenyloxycarbonyl]-2,2'-bipyridine; and
4,4'-di[(5"-F-hexyl)-4"-pentenyloxycarbonyl]-2,2'-bipyridine.

7. A complex of platinum or palladium of the formula:

$LM(II$ or $IV)$ $A^1_xA^2_y(H_2O)_z$ or $[LM(II)OH]_xA^3$ wherein
1) L represents the ligand of formula (I) according to claim 1,
2) M is platinum or palladium,
3) $A^1$ is a monovalent anionic ligand,
4) $A^2$ is a bivalent anionic ligand
5) x, y and z are defined so that
   x=0, 1, 2, 3 or 4
   y=0, 1 or 2
   z=0 or 2

$x + 2y = 2$ when the oxidation state of the metal is II; or $x + 2y = 4$ when the oxidation state of the metal is IV; and the degree of coordinance $(2 + x + 2y + z)$ is equal to 4 or 6;

6) $A^3$ represents two $A^1$ ligands or an $A^2$ ligand when x is 2, three $A^1$ ligands or a trianionic ligand when x is 3, and four $A^1$ ligands or two $A^2$ ligands when x is 4; and when $x \geq 2$, the $A^1$ can be different monovalent anions; and when $y = 2$, the $A^2$ can be different bivalent anions.

8. A complex of platinum or palladium according to claim 7, wherein z is equal to 0 and $x = 2y = 2$.

9. A complex according to any one of claims 7, wherein the anionic ligands representing $A^1$, $A^3$ or Z are selected from the group consisting of chlorides, bromides, iodides, nitrites, nitrates, carboxylates, lactates, alkoxy, aryloxy, hydrides, fluorides, acetates, trifluoroacetates, chloroacetates, cyanates, thiocyanates, azides, chlorites, hypochlorites, hypophosphites and hydroxides.

10. A complex according to any one of claims 7, wherein the anionic bivalent ligands representing $A^2$, $A^3$ or Z are selected from the group consisting of malonates, oxalates, pyrophosphites, dithiooxalates, phthalates, carboxyphtalates, gluconates, glucuronates, carbonates, sulfites, selenites, pyrosulfites, dithionites, sulfates, isocitrates and ascorbates.

11. A complex of platinum or palladium according to claim 7, wherein the trivalent ligands representing $A^3$ are selected from the group consisting of phosphates, arsenites, orthoarsenates or ferricyanides.

12. A complex of platinum or palladium according to claim 7, selected from the group consisting of:
cis-dichloro-{4,4'-di-[(12''-F-octyl)-11'-dodecenyl]-2,2'-bipyridine}-platinum (II);
cis-dichloro-{4,4'-di-[(12''-F-octyl)-11''-dodecenyl]-2,2'-bipyridine}-palladium (II);
cis-dichloro-{4,4'-di-[(12''-F-butyl)-11''-dodecenyl]-2,2'-bipyridine)}-platinum (II);
cis-dichloro-{4,4'-di-[(12''-F-butyl)-11''-dodecenyl]-2,2'-bipyridine}-palladium (II);
cis-dichloro-{4,4'-di-[(6''-F-octyl)-5''-hexenyl]-2,2'-bipyridine}-platinum (II);
cis-dichloro-{4,4'-di-[(6''-F-hexyl )-5''-hexenyl]-2,2'-bipyridine}-platinum (II);
cis-dichloro-{4,4'-di-[(11''-F-octyl)-undecenyloxycarbonyl]-2,2'-bipyridine}-platinum (II);
cis-dichloro-{4,4'-di-[(2''-F-hexyl)-ethoxycarbonyl]-2,2'-bipyridine}-platinum (II);
cis-dichloro-{4,4'-di-[(5''-F-hexyl)-pentyloxycarbonyl]-2,2'-bipyridine}-platinum (II);
cis-dichloro-{4,4'-di-[(11''-F-octyl)-10''-undecenyloxy-carbonyl]-2,2'-bipyridine}-platinum (II);
cis-dichloro-{4,4'-di-[(5''-F-hexyl)-pentenyloxy-carbonyl]-2,2'-bipyridine}-platinum (II);
cis-dichloro-{4,4'-di-[(5''-F-hexyl)-pentyloxycarbonyl]-2,2'-bipyridine}-palladium (II); and
cis-dichloro-{4,4'-di-[(11''-F-octyl)-undecyloxycarbonyl]-2,2'-bipyridine}-palladium (II).

* * * * *

UNITED STATES PATENT AND TRADEMARK OFFICE
CERTIFICATE OF CORRECTION

PATENT NO. : 5,399,694
DATED : March 21, 1995
INVENTOR(S) : Riess et al.

It is certified that error appears in the above-identified patent and that said Letters Patent is hereby corrected as shown below:

Column 21, line 21, after "d)-O-," add line --e)-C(O)--.

Column 21, line 55, change "-(CH=CH)$_c$-" to --(CH=CH)$_4$--.

Column 21, line 59, after "wherein," change "RH" to --R$_H$--.

Column 23, line 10, after "when," change "X$\geq$2," to --X $\geq$ 2--.

Column 23, line 15, after "A complex according to," change "any one of claims" to --claim--.

Column 23, line 24, after "A complex according to," change "any one of claims" to --claim--.

Column 24, line 2, change "or" to --and--.

Signed and Sealed this

Nineteenth Day of November, 1996

*Attest:*

BRUCE LEHMAN

*Attesting Officer*     *Commissioner of Patents and Trademarks*